United States Patent
Garcia et al.

(10) Patent No.: US 11,707,583 B2
(45) Date of Patent: Jul. 25, 2023

(54) DETECTION AND MONITORING OF DOSAGE DELIVERY FOR VAPORIZED WAXES, SOLIDS OR VISCOUS OILS, AND CANNABINOIDS

(71) Applicant: Arizona Board of Regents on behalf of Arizona State University, Scottdale, AZ (US)

(72) Inventors: Antonio Garcia, Chandler, AZ (US); Marco Santello, Gilbert, AZ (US); Christine Woolley, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 332 days.

(21) Appl. No.: 16/629,913

(22) PCT Filed: Jul. 11, 2018

(86) PCT No.: PCT/US2018/041685
§ 371 (c)(1),
(2) Date: Jan. 9, 2020

(87) PCT Pub. No.: WO2019/014373
PCT Pub. Date: Jan. 17, 2019

(65) Prior Publication Data
US 2021/0138166 A1 May 13, 2021

Related U.S. Application Data

(60) Provisional application No. 62/531,288, filed on Jul. 11, 2017.

(51) Int. Cl.
*A61M 15/00* (2006.01)
*A24F 40/40* (2020.01)
(Continued)

(52) U.S. Cl.
CPC ......... *A61M 15/0065* (2013.01); *A24F 40/40* (2020.01); *A24F 40/51* (2020.01);
(Continued)

(58) Field of Classification Search
CPC .......... A24F 40/40; A24F 40/51; A24F 40/53; A24F 40/10; A24F 40/60; A24C 5/3412;
(Continued)

(56) References Cited

U.S. PATENT DOCUMENTS 4,113,809 A * 9/1978 Abair .................... B06B 1/0223
261/DIG. 65
4,745,925 A  5/1988 Dietz
(Continued)

FOREIGN PATENT DOCUMENTS

DE        10312881 B3    5/2004
GB         2533653 A     6/2016
WO      WO-9600046 A1 *  1/1996 ............. A61B 5/083

OTHER PUBLICATIONS

European Patent Office. Extended European Search Report for application 18832825.6, dated Mar. 4, 2021.
(Continued)

*Primary Examiner* — Elliot S Ruddie
(74) *Attorney, Agent, or Firm* — Quarles & Brady LLP (57) ABSTRACT

A sensing module for monitoring dosage delivery of a vaporized material, and a portable vaporization unit including the sensing module, include a light sensor that detects disruptions in a light path across a vapor channel, the disruptions caused by the vaporized material flowing through the vapor channel. The light sensor includes a UV light source, which may emit 370 nm wavelength light, and a UV light detector that converts intensity of incident light in the light path into a signal. A microprocessor of the sensing module compares the signal to a baseline measure-
(Continued)

ment to determine the concentration of a medicament in the vapor; then, using the flow rate and activation time of the device, the microprocessor determines the dosage and can perform monitoring and reporting actions based on the dosage. A measuring circuit measures fluctuations in resistance/impedance of a vaporization element to further determine flow rate and/or dosage.

19 Claims, 2 Drawing Sheets

(51) Int. Cl.
*A24F 40/51* (2020.01)
*A24F 40/53* (2020.01)
*A24F 40/10* (2020.01)
*A24F 40/60* (2020.01)

(52) U.S. Cl.
CPC ........... *A24F 40/53* (2020.01); *A61M 15/008* (2014.02); *A61M 15/0021* (2014.02); *A61M 15/0086* (2013.01); *A24F 40/10* (2020.01); *A24F 40/60* (2020.01); *A61M 2205/3313* (2013.01); *A61M 2205/3334* (2013.01); *A61M 2205/50* (2013.01); *A61M 2205/8206* (2013.01)

(58) Field of Classification Search
CPC .... G01N 21/534; G01N 21/85; G01N 21/274; G01N 2201/0221; G01N 21/33; G01N 21/39; A61M 15/0065; A61M 15/0021; A61M 15/008; A61M 15/0086; A61M 2205/3313; A61M 2205/3334; A61M 2205/50; A61M 2205/8206; A61M 11/042
USPC .................................................... 128/200.23
See application file for complete search history.

(56) References Cited

U.S. PATENT DOCUMENTS

| | | | |
|---|---|---|---|
| 6,275,650 | B1 | 8/2001 | Lambert |
| 6,606,989 | B1 | 8/2003 | Brand et al. |
| 7,451,760 | B2 | 11/2008 | Denyer et al. |
| 8,182,443 | B1 | 5/2012 | Kiani |
| 8,910,630 | B2 | 12/2014 | Todd |
| 9,041,925 | B2 | 5/2015 | Adamo et al. |
| 2003/0025086 | A1* | 2/2003 | Stroka .................... G01N 30/95 |
| | | | 356/417 |
| 2003/0137648 | A1* | 7/2003 | Van Voorhis ............. G01P 3/36 |
| | | | 356/28.5 |
| 2005/0068528 | A1 | 3/2005 | Altobelli |
| 2017/0095005 | A1* | 4/2017 | Monsees ............. A61M 11/042 |
| 2017/0156399 | A1* | 6/2017 | Freeman ................ A24F 40/50 |

OTHER PUBLICATIONS

International Searching Authority. International Search Report and Written Opinion for application PCT/US2018/041685, dated Sep. 27, 2018.

* cited by examiner

FIG. 3

DETECTION AND MONITORING OF DOSAGE DELIVERY FOR VAPORIZED WAXES, SOLIDS OR VISCOUS OILS, AND CANNABINOIDS

CROSS REFERENCE TO RELATED APPLICATIONS

This application is a U.S. National Stage of PCT Application No. PCT/US2018/041685 filed on Jul. 11, 2018 which claims the benefit of U.S. Provisional Patent Application No. 62/531,288, filed on Jul. 11, 2017, the entire contents of which are incorporated herein by reference.

BACKGROUND

Lung inhalation of airborne, vaporized medications is a means for drug delivery noted for fast action, non-invasiveness, and more patient compatibility as compared to injection, ingestion, and transdermal modes. Indication for inhalation delivery is desired especially for patients suffering from nausea or those requiring fast pain relief in settings where needle use is inconvenient or undesired. For vaporized medication delivery at the desired therapeutic level, it is important to quantify and control the dosage being inhaled by the patient. In the present state of the art, for the delivery of vaporized waxes and oils, such as cannabinoids, dosage is often calibrated to the user based on patient observation that a desired physiological or psychodynamic response is achieved rather than on the delivery of a metered amount of medication. A device that detects and measures the amount of medication that is being delivered to the patient via inhalation of vaporized substances is desired.

Existing approaches fail to achieve the desired dosage detection and measurement of inhaled substances. One known system teaches the use of an optical sensor to monitor breath dependent airflow through a device. This early art describes monitoring changes in a transmitted or reflected optical signal of a particular type, but does not specify the use of UV detection or the controlled delivery of medication to a patient. Another early system uses an inhalation sensor to monitor apnea and to dispense a therapeutic gas. Inhalation is monitored using an optoelectronic sensor and measures airflow directly in an airway passage. It does not teach the use of a portable sensor or method for monitoring the dosage of a medication delivered. Another example teaches the controlled delivery of a vaporized liquid or treatment gas to a person or animal using an optical sensor. Differences in optical absorption are used to monitor the flow of gas and signals are sent to a control unit on the device to regulate the delivery to a patient. This device does not teach the use of a portable sensor on a portable device. Another system uses a device for administering a medical aerosol via inhalation. Electronic controls allow the atomization time and interval to be set for medication delivery, which is triggered through a pressure sensor responding to suction at the mouthpiece. However, this system does not include dosage control or non-pressure sensing of dosage delivered to the patient.

More recent art describes the control of drug delivery using a nebulizer. The nebulizer calculates the dose of the drug a patient receives in their lungs and is supplied with a pre-programmed dose of the needed drug. Once the prescribed amount is delivered, an airflow sensor, calibrated to each patient, stops the atomization of more drug regardless of whether the nebulizer is empty. The device must then be reset before a next dose can be taken. Another system uses a respiration hose for a medical respiration apparatus. An optical sensor is used where the signal line extends the length of the hose to detected transmission between the sensor device and respiration apparatus. It does not teach the control of medical dosage or delivery of a medicinal wax or oil. Another existing drug administration controller includes a sensor that monitors a physiological parameter in order to signal the administration device to affect treatment by initiating medication, adjusting the dosage, or stopping the administration of drugs. It does not teach the delivery of a defined amount of medication to the patient.

In particular, technology enabling the medical administration of cannabinoids to patients does not teach a device that regulates or meters dosage for a patient. Systems and methods of a portable vaporized substance delivery device that uses optical sensing configurations to detect and measure dosages of the substance are described herein.

SUMMARY

The present disclosure overcomes the aforementioned drawbacks by providing devices and methods that use a light sensor, such as a UV sensor, to monitor and control the dosage of medicinal waxes and heavy oils from a single cartridge. In particular, the dosage of vapor delivered can be monitored and recorded using UV light provided and detected by the present device. The UV sensor may include a UV LED light source with maximum intensity at 370 nm and a UV light detector which is connected to a voltage measuring device. The light source and detector are fixed in a modular body that may be connected to a portable vaporizing unit between the vaporization chamber and the mouthpiece. Disruption of the light path to the detector allows the monitoring of the vaporized dosage delivered to the patient. Since the power requirement of the sensor can be met by a low energy source and due to the desired feature of portability, the sensor may be battery powered.

When power is supplied to the sensor, the output signal initially registers a high reading. Vaporization of a medicinal wax or heavy oil disrupts the light path between the LED and the detector, causing a rapid reduction in the output signal. Once vaporization is stopped, the recovery of the sensor to a baseline reading occurs rapidly since the path no longer contains a sufficient amount of vapor to disrupt the light path. Monitoring information can be used in a control system to meter the amount inhaled by the patient. The monitoring of this vaporized dosage can be displayed, analyzed and adjusted through accompanying encrypted software. The software is designed to give the user and their accompanying health care professional better control over their treatment.

The foregoing and other advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Embodiments of systems, devices, and methods in accordance with the present disclosure provide detection, measurement, and monitoring of a dosage of a vaporized material delivered to a patient via direct lung inhalation. Such a device may be an inhaler configured to vaporize a medicinal material, including a wax and/or a heavy oil. In particular, the material may contain cannabinoids, and the device may be configured to measure a dosage based on the presence of cannabinoids in the produced vapor. The device may include a light sensor, such as a battery-powered UV sensor, positioned so that the vapor passes across or through, or otherwise contacts or interacts with, the sensor as the vapor is inhaled by the patient. The sensor may include a light detector and a light generator that emits light onto the light detector. The sensor detects and/or measures the presence and/or composition of the vapor based on variations in the light incident upon the light detector. The present methods of UV detection for vapor analysis constitute new art in drug delivery monitoring, since existing systems use sensors that have employed other detection mechanisms.

Four advantages, among others, of employing UV light for detection of these vapors are described here. First, a shorter wavelength of light will scatter more than longer wavelengths of light, such as visible and infrared light, thus yielding a signal that has a higher sensitivity to low concentrations of droplets and particles suspended in the inhaled vapor stream. Secondly, cannabinoids and other medicinal oils and waxes are organic molecules that can absorb significantly more UV light per molecule than light in the visible or infrared range. Absorption of UV light by the molecules in the vapor can then be used to sense vapor inhaled by the patient that is particle or droplet free. The third advantage is in the rapid recovery time of a light-path sensor as compared to gas sensors that rely on a change in impedance or resistance of a metal film due to adsorption to the sensor surface. The light-sensor can recover very quickly because it measures molecules in the UV light path, whereas a metal film sensor recovers slowly due to the heat needed to vaporize heavy oils and waxes from the surface of the sensor. A fourth advantage is that UV light sensors are subject to less interference by external visible light and infrared light (e.g., heat) as compared to visible and infrared light sensors since they operate at wavelengths of light that are found at very low intensities indoors and outdoors. Interference from light sources may be further reduced by orienting the sensor and surrounding structures so that the UV light path is well defined; in particular, no mirrors or other reflective surfaces are used.

Figure 1:
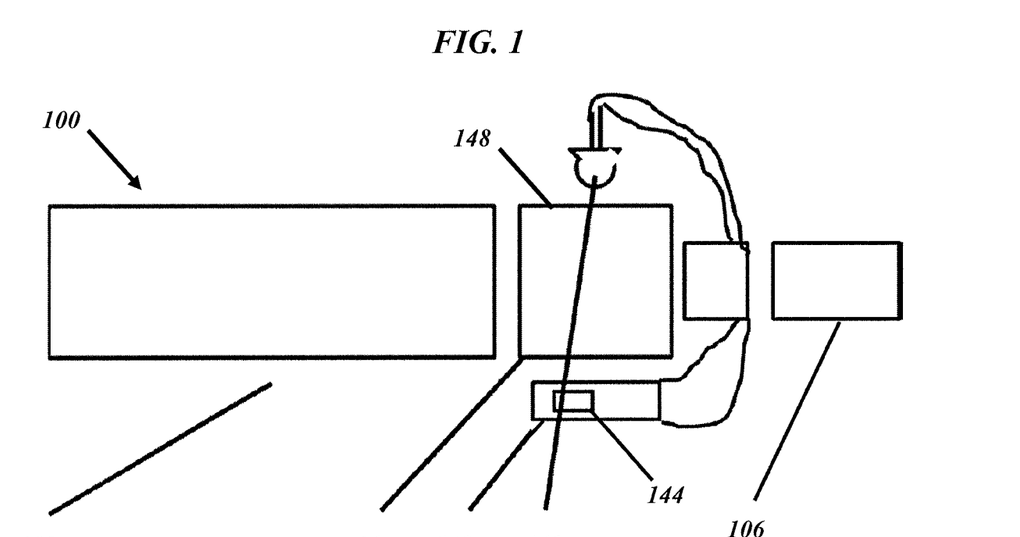
FIG. 1 is a diagram of an exploded view of an example vaporization device in accordance with the present disclosure.
Figure 2:
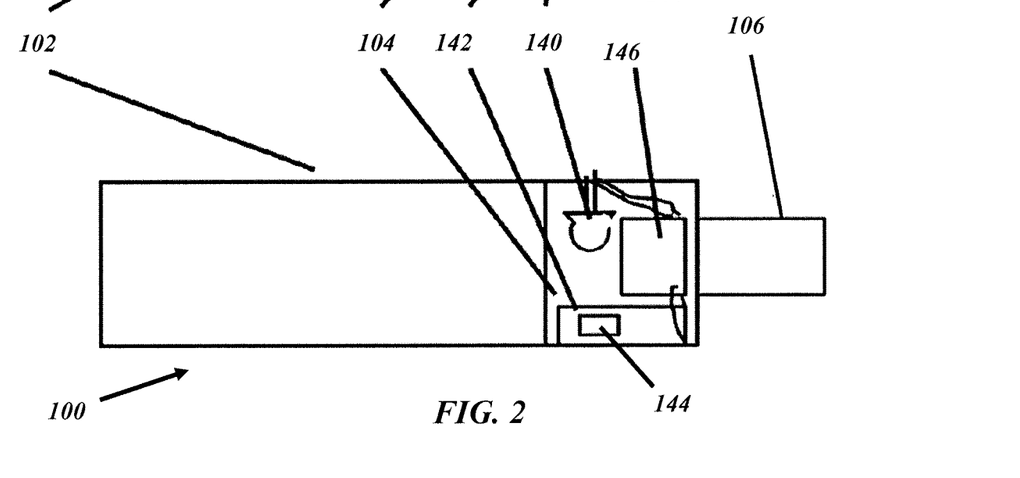
FIG. 2 is a diagram of the vaporization device of FIG. 1, assembled.

Referring to FIGS. 1 and 2, an exemplary vaporization device 100 may be portable, in that the device 100 has dimensions that facilitate a patient easily carrying the device 100 and keeping the device 100 within reach throughout the day. A portable device 100 can range in size from pocket-sized, to handheld, to a larger size that fits in a purse or carryall, and to a bag-sized (e.g., backpack-sized) device that nevertheless is still easy for the patient to carry. Non-limiting exemplary dimensional configurations of the device 100 can be identified with reference to existing inhaler and/or vaporizing devices, such as: cartridge-based handheld medicinal (e.g., asthma) inhalers; electronic cigarettes and electronic pipes of various configurations; other handheld vaporizers for oils, waxes, and/or plant material; tabletop nebulizers; and, the like.

The vaporization device 100 may include a body 102 that contains a wax, oil, or other material to be vaporized. The body 102 may, in some embodiments, be a cartridge, and may be refillable and/or disposable. The body 102 may be permanently or removably attached to a sensor module 104. A vaporizing element (see FIG. 3), such as a nichrome wire connected to a source of electrical current (e.g., a battery 146), may be disposed in one or both of the body 102 and the sensor module 104, or between the body 102 and the sensor module 104. In some embodiments, during operation, the device 100 conducts the material out of the body 102 to the vaporizing element, converting the material into vapor. Some or all of the vapor may then be conducted into the sensor module 104 due to a suction force applied by a user.

In other embodiments, the material is conducted into the sensor module 104 and to the vaporizing element. The sensor module 104 may include a sensing arrangement capable of detecting the presence and/or composition of the vapor. The vaporizing element may be positioned near the sensing arrangement, such that the produced vapor passes (e.g., is pulled by the suction force) into the sensing arrangement. In some embodiments, the sensing arrangement may be based on UV electromagnetic wavelength detection. As illustrated, the sensing arrangement may include a UV light source 140, such as one or more light-emitting diodes, and a UV light detector 142 positioned so that UV light emitted by the UV light source 140 is incident upon an active area 144 of the UV light detector 142. In some embodiments, the UV light detector 142 may generate a signal representing the intensity of incident light; for example, the signal may be a voltage that varies proportionally with the light intensity. The sensing arrangement may include a vapor channel with a known structure (e.g., height, width, etc.). The vapor channel may extend from the vaporizing element through the light path between the UV light source 140 and the active area 144. The width, height, and other dimensions of the vapor channel may correspond to the size of the active area 144; this correspondence of dimensions can be used to calculate the volume (e.g., of vapor) contained by the light path, as described below.

The sensor module 104 may further include an onboard power supply, such as a battery 146, which electrically connects to and powers the UV light source 140 and/or the UV light detector 142. Other components of the sensor module 104 that are not illustrated may include, for example: a microprocessor configured to electrically connect (e.g., via wires, conductive traces, pins, and the like) to, or otherwise being in electrical communication with, the light sensor for processing sensor data generated by the UV light detector 142; a transmitter, receiver, and/or transceiver configured to electrically connect to, or otherwise being in electrical communication with, the light sensor and/or the microprocessor, for transmitting recorded and/or processed data and/or for receiving parameters, settings, and/or instructions; and, a display configured to electrically connect to, or otherwise being in electrical communication with, the light sensor and/or the microprocessor, for displaying to the patient, a physician, or another person status information such as dosage, usage history, contents and/or number of uses left in a cartridge, and the like. A housing 148 of the sensor module 104 may enclose, encapsulate, contain, cover, or otherwise protect and/or support the other components of the sensor module 104. The housing 148 may have one or more portals for gaining access to the components inside, such as a battery door for replacing the battery 146. The housing 148 may also include structures, such as interior walls, that define the vapor channel.

A mouthpiece 106 may permanently or removably attach to the sensor module 104, completing a vapor channel from the vaporizing element through the sensor module 104 and to the patient inhaling through the mouthpiece 106. In operation, the sensing arrangement may form a UV light path, between the UV light source 140 and the UV light detector 142, which intersects, crosses, or otherwise contacts the portion of the vapor channel that is in the sensor module 104. A baseline measurement of the intensity of UV light received at the UV light detector 142 is stored in the device 100, or is recorded upon activation of the sensing arrangement. The baseline measurement indicates how much UV light is transmitted across the vapor channel and received by the UV light detector 142 when there is no vapor present in the vapor channel. Then, one or more active measurements of the received light intensity are obtained and recorded while vapor is being conducted through the vapor channel (i.e., the patient is inhaling from the device 100). Processing elements, which may be on the device 100 as described above or may be remote from the device 100 and may receive the recorded data from the device 100, then compare the active measurements to the baseline measurements and/or to each other to determine one or more characteristics of the vapor, such as its composition, volume, flow rate, and the like.

Figure 3:
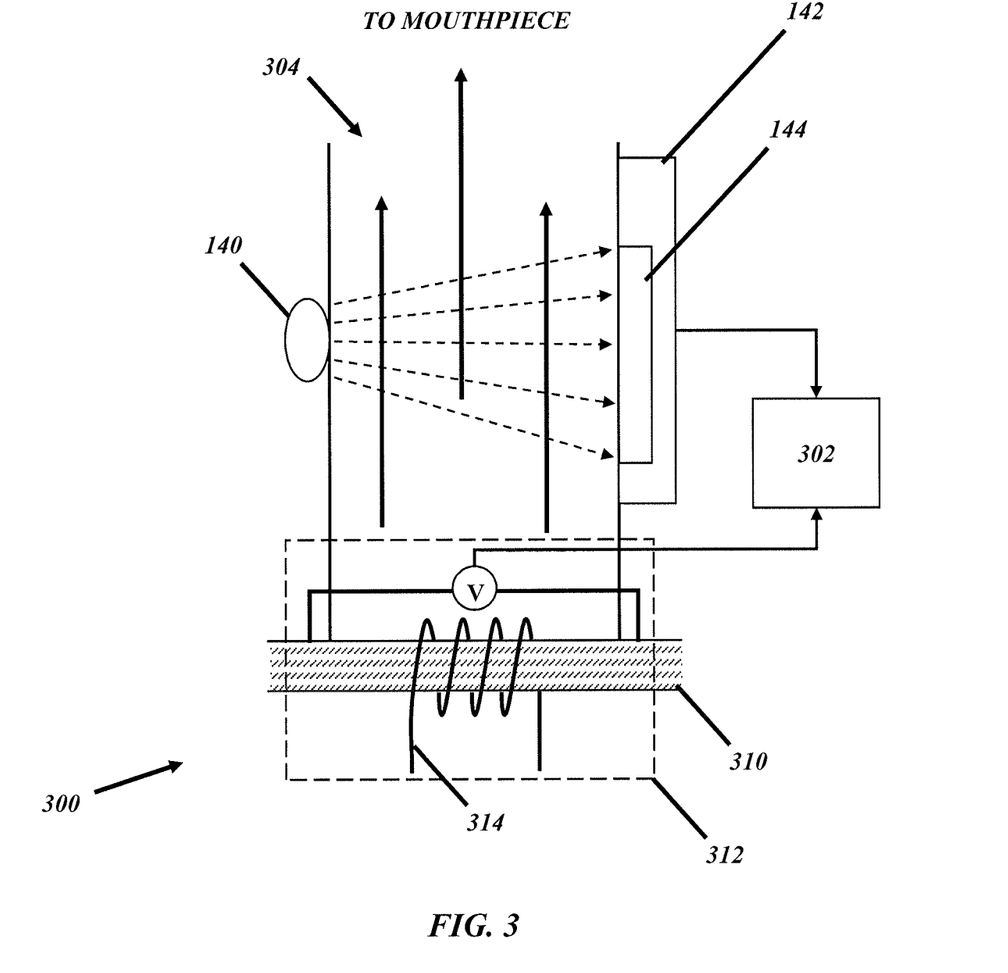
FIG. 3 is a diagram of a portion of another example vaporization device in accordance with the present disclosure.

FIG. 3 is a component abstraction 300 of part of an inhalation device constructed in accordance with the present disclosure, such as the device 100 of the previous Figures. The abstraction 300 shows that a microprocessor 302 may be included in the device, and may process signals generated by one or more sensing arrangements. For example, the microprocessor 302 may receive the output signal of the UV detector 142 representing light from the source 140 that traverses the vapor channel 304 and is incident on the active area 144 of the UV detector 142. Additionally or alternatively, the sensing module may include a measurement circuit 312 that measures changes in the resistance of the device's heating element 310 (e.g., a nichrome wire). It has been determined that the heating element 310 resistance fluctuates as the heating element 310 vaporizes the medicament. The microprocessor 302 may be configured to use the measurement circuit 312 to obtain one or more baseline resistance measurements when the device is not vaporizing a compound; then, the microprocessor 302 may measure the fluctuating resistance during use, and may determine characteristics such as flow rate and dosage based on the fluctuations. In some embodiments, such as when the heating element 310 is in a DC circuit, the heating element 310 resistance may be directly measured by the measurement circuit 312. In other embodiments, such as the illustrated example, the measurement circuit 312 may include an inductor 314 positioned so that the resistance fluctuations in the heating element 310 cause corresponding and proportional fluctuations in the inductive reactance of the inductor 314. The measurement circuit 312 thus may detect fluctuations in impedance and report them to the microprocessor 302.

Accompanying and/or subsequent calculations may be made based on current and/or historical data from the sensing arrangement. In particular, from data describing the flow rate and composition of the vapor, the present device may determine (or may be used to determine) a dosage of a medicant contained in the vaporizable material, the dosage being, for example, an amount (e.g., in milligrams or milliliters) of the medicant delivered to the patient during one inhalation on the device. In various embodiments described herein and in the examples below, the medicant may be a composition of cannabinoids, which have been shown to absorb and/or scatter a very high percentage of incident UV light waves. The absorption and scattering properties of cannabinoids and/or other particles in the vapor can be predetermined and stored/used by the device (e.g., by a processor connected to the UV sensor) to calibrate the sensor and to determine one or more particle concentrations in the portion of the vapor column disposed within the light path at any particular moment in time.

The dosage may be characterized as an amount of the medicament or vaporized material that is received by a user inhaling the vapor column through the mouthpiece of the device; alternatively, the dosage may be characterized as an amount of the medicament or vaporized material that exits the mouthpiece in the direction of the inhaling user during the operating time. In one embodiment, a microprocessor of the device may be configured to calculate or estimate the dosage by multiplying the calculated concentration by an operating time and a flow rate to produce the dosage (or an estimate of the dosage). The operating time may be the length of time that the device generates the vapor column, and may, for example, be one or more of: a duration of the user's inhalation, measured using a pressure sensor, flow sensor, or other sensor of the device; a preset duration that the device generates vapor when activated; a duration that the UV sensor senses vapor in the light path; a duration that the medicament and/or vapor column is exiting the mouthpiece in the direction of a user inhaling the vapor column through the mouthpiece; or another duration. The flow rate of the vapor through the light path may be detected by a flow sensor, or may be a predetermined and/or estimated baseline flow rate calculated from the volume of the light path/channel (e.g., area of cross-section of light path times channel height) and an estimate of the typical suction pressure of about 2-3 psi for a person using the device. A microprocessor of the inhalation device may further be configured with one or more triggers that cause the microprocessor to deactivate the heating element or otherwise disable the device when certain measurements are obtained. For example, the device may be deactivated after a predetermined operating time has elapsed, or once a predetermined dosage is reached.

EXAMPLES

Example 1

Detection of Methanol Vapor Heated in a Test Tube

A 1 mL sample of methanol was placed in a glass test tube with a boiling stone. A direct flame was used to heat the test tube and produce a strong vapor column. The test tube was aligned with the bottom of the UV sensor housing so that the vapor column was directed between the 370 nm LED light source and the detector, thereby disrupting the passage of light between the two. In the presence of a strong column of methanol vapor, a 16% decrease in the signal was observed within 2 seconds. Recovery of the sensor to a baseline reading of 180 mV was observed within 5 seconds once the vapor was stopped.

Example 2

Detection of Acetone Vapor Heated in a Test Tube

A 1 mL sample of acetone was placed in a glass test tube with a boiling stone. Direct flame was used to heat the test tube and produce a strong vapor column that was fed directly into the bottom of the UV sensor housing, allowing the vapor column to pass between the LED light source and light detector. In the presence of vapor the sensor showed rapid detection of the sample, demonstrating a 100% disruption of the signal within 2 seconds. Recovery of the sensor to a baseline reading of 180 mV was observed within 5 seconds after the presence of vapor was removed.

Example 3

Detection of Isopropanol Vapor Heated in a Test Tube

A 1 mL sample of acetone was placed in a glass test tube with a boiling stone. Direct flame was used to heat the test tube and produce a strong vapor column. The test tube was aligned with the bottom of the UV sensor housing, feeding the vapor column directly between the LED light source and light detector. In the presence of a strong vapor column the sensor demonstrated rapid detection of the sample, showing a 27% disruption of the signal within 2 seconds. Recovery of the sensor to a baseline reading of 180 mV occurred within 5 seconds of vapor removal.

Example 4

Ethanol does not Produce a Change in Sensor when Heated in Test Tube

A 1 mL sample of ethanol was placed in a glass test tube with a boiling stone. Direct flame was used to heat the test tube and produce a vapor column. The test tube was aligned with the bottom of the UV sensor housing, feeding the vapor directly between the LED light source and light detector. As predicted by the small absorbance peak produced by liquid ethanol at the shorter wavelength of 250 nm, there was no significant influence on the signal output from the sensor. Deposition of liquid droplets on the epoxy surface of the LED showed a change of less than 5% in the sensor readings and fluctuated both above and below the baseline of 180 mV. Removal of the sample and the evaporation of condensation on the LED allowed the sensor to return to stable baseline readings within 30 seconds.

Example 5

Detection of Water Vapor Heated in a Small Beaker

A 5 mL sample of water was placed in a 10 mL glass beaker and heated using a hotplate. When vigorous boiling was observed, the beaker was moved from the hotplate and held below the housing of the UV sensor. Vapor was directed into the channel between the LED light source and light detector. The column of water vapor caused a 46% disruption of the signal within 2 seconds and recovery upon sample removal was very rapid (less than 5 seconds).

Example 6

Detecting Coconut Oil Vapor Produced by Portable Vaporization Device

Approximately 150 mg of coconut oil was deposited into the sample reservoir of a portable vaporization device. Upon the application of power to the device, a vigorous vapor column was observed immediately (less than 2 seconds). The vapor column was directed into the housing of the UV sensor and allowed to pass between the LED light source and light detector. The presence of coconut oil vapor produced a 28% disruption of the signal output, observed to take place instantly (less than 2 seconds). Recovery of the sensor was near instantaneous (less than 2 seconds) once vaporization was stopped.

Example 7

Detecting Cannabinoid Vapor Produced by Portable Vaporization Device

Approximately 150 mg of viscous cannabinoid oil was deposited into the sample reservoir of a portable vaporization device. Upon the application of power to the device, vapor was observed immediately (less than 2 seconds). The vapor column was directed into the housing of the UV sensor and allowed to pass between the LED light source and light detector. The presence of cannabinoid vapor produced a 100% disruption of the signal output, observed to take place instantaneously (less than 2 seconds). Recovery of the sensor was rapid (less than 10 seconds), but incomplete due to deposition on the epoxy surface of the LED. Cleaning of the LED surface resulted in 100% sensor recovery to baseline.

Example 8

Device Does Not Detect Eucalyptus Vapor Heated in a Test Tube

A 1 mL sample of eucalyptus oil was placed in a glass test tube with a boiling stone. Direct flame was used to heat the sample. It was observed that vapor was produced from the heating, but it did not rise as rapidly or as high in the tube, as was the case for vapors produced using lower boiling point materials. No change in the UV detector was noted for the heating of eucalyptus oil, because the direct flame did not result in sufficient heating to produce a significant vapor column allowing the disruption of signal.

Example 9

Device Does not Detect Vapor of Coconut Oil Boiled in a Test Tube

A 150 mg sample of coconut oil was placed in a glass test tube with a boiling stone. Direct flame was used to heat the sample. Phase change from a solid to liquid oil sample was observed and vapor could be visualized in the test tube. The vapors did not rise as rapidly or as highly in the tube as those produced using lower boiling point materials. No change in the UV detector was noted for the heating of coconut oil in a test tube, because the direct flame did not result in sufficient heating to produce a significant vapor column allowing the disruption of signal.

In various embodiments the invention provides a vaporization device having one or more of the following example features:
 1. A sensor to monitor a vigorous column of vaporized material
  a. A sensor to monitor the dosage of vaporized medications delivered
  b. A control unit to record the history of dosage delivered
  c. A sensor to detect light scattering from a vigorously vaporized material d. A sensor capable of sensing the presence of vapor immediately (less than 2 seconds)

e. A sensor capable of rapid recovery when vaporization is stopped (less than 10 seconds)

f. A sensor that is not prone to fouling or baseline drift from the deposition of vaporized compounds 2. A UV sensor for monitoring vapor consisting of a 370 nm LED light source and sensor to detect changes in voltage experienced when vapor disrupts the light path 3. A UV sensor that can measure vapor for cannabinoids at 0.08 mg/mL concentration in air 4. A UV sensor that can measure cannabinoid vapor and cannabinoid particulates or small droplets in air 5. A UV sensor that can measure vaporized medicines and vaporized medicine particulates or small droplets in air 6. A UV sensor that can operate at ambient temperatures from 20 degrees Fahrenheit to 120 degrees Fahrenheit 7. A UV sensor that can operate in a humidity range of 2% to 90% humidity 8. A UV sensor that has an operating lifetime of over 1,000 hours 9. A UV sensor that is not sensitive to the presence of a magnetic field 10. A UV sensor that will work with a current/voltage sensor and that can detect power to a device 11. A UV sensor that is not affected by sudden movement of the portable device 12. A UV sensor that is portable, able to fit in one's pocket, weighs less than 10 g, and is battery powered using two watch batteries.

In another aspect, the presently described invention provides a device that includes: a housing connectable to a vaporization chamber and a mouthpiece to form a portable vaporizing unit including a vapor channel that conducts vaporized material from an end of the vaporization chamber through the housing and the mouthpiece; an ultraviolet (UV) light sensor disposed at least partially within the housing and electrically connected to a power supply, the UV light sensor including a UV light source and a UV light detector spaced from the UV light source to form a light path that traverses the vapor channel, the UV light detector including an active area on which light emitted from the UV light source into the light path is incident, and the UV light detector, when powered by the power supply, generating a first signal representing an intensity of the light incident on the active area; and, a microprocessor disposed in the housing and electrically connected to the UV light sensor.

The microprocessor is configured to electronically perform the steps of: receiving the first signal for an operating time during which a vapor column comprising the vaporized material flows through the vapor channel; determining, based on the first signal, a reduction of the intensity of the light incident on the active area, the reduction being relative to a baseline measurement of the intensity when there is no disruption of the light in the light path; determining, based on the reduction and one or more properties of a medicament, a concentration of the medicament within the vaporized material; calculating, based at least in part on the concentration, the operating time, and a flow rate of the vapor column through the vapor channel, a dosage of the medicament received by a user inhaling the vapor column through the mouthpiece; and, performing at least one action based on the dosage.

The device may further include a battery disposed in the housing and electrically connected, as the power supply, to the UV light source and the UV light detector. The microprocessor may store, as the one or more properties of the medicament, UV light absorption and UV light scattering properties of one or more cannabinoids. The device may further include a display supported by the housing, the display displaying status information associated with usage of the portable vaporization device; the at least one action based on the dosage may include executing encrypted software to generate monitoring information based on the dosage and cause the display to include the monitoring information in the displayed status information.

In addition to or instead of the light sensor, a device in accordance with the invention may include: a vaporizing element that vaporizes material contained in the vaporization chamber to produce the vaporized material, the vaporizing element positioned, when the housing is connected to the vaporization chamber, to receive the material as the material is drawn out of the end of the vaporization chamber and to conduct the vaporized material into the vapor channel; and, a measurement circuit in electronic communication with the microprocessor and in electric communication with the vaporizing element, the measurement circuit detecting fluctuations in one or both of the resistance and the impedance of the vaporizing element, producing fluctuation data representing the detected fluctuations, and sending the fluctuation data to the microprocessor, the microprocessor calculating the dosage based on the fluctuations detected during the operating time.

In yet another aspect, the presently described invention provides a device for monitoring dosage delivery of a medicament, the device including: a portable housing defining at least a portion of a vapor channel; a light sensor measuring an intensity of light transmitted across the vapor channel and producing sensor data representing the measured intensity; and, processing means in electrical communication with the light sensor, the processing means having a configuration for receiving the sensor data for an operating time during which a vapor of the medicament flows through the vapor channel, determining, based at least in part on the operating time and the measured intensity represented by the sensor data, a dosage of the medicament, and performing at least one action based on the dosage. The light measured by the light sensor may be ultraviolet (UV) light and the medicament may absorb or scatter a portion of incident UV light that impinges the medicament, the portion being detectable by the light sensor. The light sensor may include a UV light detector having an active area and measuring the intensity based on the light incident on the active area, and a UV light source emitting the light across the vapor channel and onto the UV light detector. The light emitted by the UV light source may have a maximum intensity at a wavelength of 370 nanometers.

To determine the dosage, the processing means may: determine the measured intensity based on the sensor data; compare the measured intensity to a baseline measurement representing the intensity measured by the light sensor when the vapor channel is empty to determine a disruption of the light caused by the vapor flowing through the vapor channel; and determine, using predetermined UV light absorption and UV light scattering properties of the medicament, a concentration of the medicament in the vapor. The device may further include a flow sensor measuring a flow rate of the vapor through the vapor channel and producing flow data representing the measured flow rate; to determine the dosage, the processing means may obtain the flow data, determine the measured flow rate based on the flow data, and calculate the dosage based on the concentration, the measured flow rate, and the operating time. The medicament may comprise one or more cannabinoids, and the light sensor may be configured to detect the disruption of the light associated with the concentration (of the one or more cannabinoids) being as low as 0.08 mg/mL in air.

The device may further include a measurement circuit in electric communication with a vaporizing element that vaporizes a material comprising the medicament to produce the vapor, the measurement circuit measuring fluctuations in one or both of the resistance and the impedance of the vaporizing element and producing fluctuation data representing the measured fluctuations; to determine the dosage, the processing means may further obtain the fluctuation data, determine the measured fluctuations based on the fluctuation data, and calculate the dosage further based at least in part on the measured fluctuations. The vaporizing element may be powered by a direct current circuit, and the measurement circuit may directly measure the resistance of the vaporizing element. The measurement circuit may include an inductor positioned with respect to the vaporization element so that fluctuations in the resistance of the vaporization element cause corresponding and proportional fluctuations in the inductive reactance of the inductor, the fluctuation data representing the measured fluctuations in impedance based on the fluctuations in the inductive reactance.

The device may further include one or more batteries disposed in the housing, the one or more batteries electrically connected and providing power to the light sensor and the processing means. The one or more batteries may be further electrically connected and provide power to a vaporizing element that vaporizes a material comprising the medicament to produce the vapor. The at least one action may include obtaining a dosage history for a user, updating the dosage history to include the dosage, and recording the updated dosage history.

The housing of the device may include: a first end that connects to a body that defines a vaporization chamber for containing a material comprising the medicament; and, a second end that connects to a mouthpiece and cooperates with the mouthpiece to form the vapor channel, the body, housing, and mouthpiece, when connected, forming a portable vaporization unit, a user of the portable vaporization unit inhaling the vapor through the mouthpiece, the at least one action including monitoring, based on the dosage, the user's usage of the portable vaporization unit. The device may include: a body permanently or removably attached to the housing, the body defining a vaporization chamber for containing a material comprising the medicament; and, a mouthpiece permanently or removably attached to the housing and cooperating with the housing to form the vapor channel, the body, housing, and mouthpiece, when connected, forming a portable vaporization unit, a user of the portable vaporization unit inhaling the vapor through the mouthpiece, the at least one action including monitoring, based on the dosage, the user's usage of the portable vaporization unit.

The present invention has been described in terms of one or more preferred embodiments, and it should be appreciated that many equivalents, alternatives, variations, and modifications, aside from those expressly stated, are possible and within the scope of the invention.

What is claimed is:

1. A device comprising:
    a housing connectable to a vaporization chamber and a mouthpiece to form a portable vaporizing unit including a vapor channel that conducts vaporized material from an end of the vaporization chamber through the housing and the mouthpiece;
    an ultraviolet (UV) light sensor disposed at least partially within the housing and electrically connected to a power supply, the UV light sensor comprising a UV light source and a UV light detector spaced from the UV light source to form a light path that traverses the vapor channel, the UV light detector comprising an active area on which light emitted from the UV light source into the light path is incident, and the UV light detector, when powered by the power supply, generating a first signal representing an intensity of the light incident on the active area;
    a vaporizing element that vaporizes material contained in the vaporization chamber to produce the vaporized material;
    a measurement circuit in electronic communication with the vaporizing element, the measurement circuit producing fluctuation data representing measured fluctuations in one or both of a resistance and an impedance of the vaporizing element; and
    a microprocessor disposed in the housing and electrically connected to the UV light sensor, wherein the microprocessor:
        receives the first signal for an operating time during which a vapor column comprising the vaporized material flows through the vapor channel;
        determines, based on the first signal, a reduction of the intensity of the light incident on the active area, the reduction being relative to a baseline measurement of the intensity when there is no disruption of the light in the light path;
        determines, based on the reduction and one or more properties of a medicament, a concentration of the medicament within the vaporized material;
        obtains, from the measurement circuit, the fluctuation data; and
        calculates, based at least in part on the concentration, the operating time, the fluctuation data, and a flow rate of the vapor column through the vapor channel, a dosage of the medicament received by a user inhaling the vapor column through the mouthpiece; and
        performs at least one action based on the dosage.

2. The device of claim 1, further comprising a battery disposed in the housing and electrically connected, as the power supply, to the UV light source and the UV light detector.

3. The device of claim 1, wherein the microprocessor stores, as the one or more properties of the medicament, UV light absorption and UV light scattering properties of one or more cannabinoids.

4. The device of claim 1, further comprising a display supported by the housing, the display displaying status information associated with usage of the portable vaporization device, the at least one action including executing encrypted software to:
    generate monitoring information based on the dosage; and
    cause the display to include the monitoring information in the displayed status information.

5. A device for monitoring dosage delivery of a medicament, the device comprising:
    a portable housing defining at least a portion of a vapor channel;
    a light sensor measuring an intensity of light transmitted across the vapor channel and producing sensor data representing the measured intensity;
    processing means in electrical communication with the light sensor, wherein the processing means:

receives the sensor data for an operating time during which a vapor of the medicament flows through the vapor channel;

determines, based at least in part on the operating time and the measured intensity represented by the sensor data, a dosage of the medicament; and performs at least one action based on the dosage; and a measurement circuit in electrical communication with a vaporizing element that vaporizes a material comprising the medicament to produce the vapor, the measurement circuit measuring fluctuations in one or both of the resistance and the impedance of the vaporizing element and producing fluctuation data representing the measured fluctuations;

wherein to determine the dosage, the processing means further:

obtains the fluctuation data;

determines the measured fluctuations based on the fluctuation data; and calculates the dosage further based at least in part on the measured fluctuations.

6. The device of claim 5, wherein the light measured by the light sensor is ultraviolet (UV) light and the medicament absorbs or scatters a portion of incident UV light that impinges the medicament, the portion being detectable by the light sensor.

7. The device of claim 6, wherein the light sensor comprises:

a UV light detector having an active area and measuring the intensity based on the light incident on the active area; and a UV light source emitting the light across the vapor channel and onto the UV light detector.

8. The device of claim 7, wherein the light emitted by the UV light source has a maximum intensity at a wavelength of 370 nanometers.

9. The device of claim 6, wherein to determine the dosage, the processing means:

determines the measured intensity based on the sensor data;

compares the measured intensity to a baseline measurement representing the intensity measured by the light sensor when the vapor channel is empty to determine a disruption of the light caused by the vapor flowing through the vapor channel; and determines, using predetermined UV light absorption and UV light scattering properties of the medicament, a concentration of the medicament in the vapor.

10. The device of claim 9, wherein the medicament comprises one or more cannabinoids and the light sensor is configured to detect the disruption of the light associated with the concentration being as low as 0.08 mg/mL in air.

11. The device of claim 5, wherein the vaporizing element is powered by a direct current circuit, and the measurement circuit directly measures the resistance of the vaporizing element.

12. The device of claim 5, wherein the measurement circuit comprises an inductor positioned with respect to the vaporization element so that fluctuations in the resistance of the vaporization element cause corresponding and proportional fluctuations in the inductive reactance of the inductor, wherein the fluctuation data represents the measured fluctuations in impedance based on the fluctuations in the inductive reactance.

13. The device of claim 5, further comprising one or more batteries disposed in the housing, the one or more batteries electrically connected and providing power to the light sensor and the processing means.

14. The device of claim 13, wherein the one or more batteries are further electrically connected and provide power to the vaporizing element.

15. The device of claim 5, wherein the at least one action comprises obtaining a dosage history for a user, updating the dosage history to include the dosage, and recording the updated dosage history.

16. The device of claim 5, wherein the housing comprises:

a first end that connects to a body that defines a vaporization chamber for containing the material comprising the medicament; and a second end that connects to a mouthpiece and cooperates with the mouthpiece to form the vapor channel;

wherein the body, housing, and mouthpiece, when connected, form a portable vaporization unit.

17. The device of claim 5, further comprising:

a body permanently or removably attached to the housing, the body defining a vaporization chamber for containing the material comprising the medicament; and a mouthpiece permanently or removably attached to the housing and cooperating with the housing to form the vapor channel;

wherein the body, housing, and mouthpiece, when connected, form a portable vaporization unit.

18. The device of claim 1, wherein the microprocessor calculates the dosage of the medicament by multiplying the concentration by the operating time and the flow rate.

19. A device for monitoring dosage delivery of a medicament, the device comprising:

a portable housing defining at least a portion of a vapor channel;

a vaporizing element configured to vaporize a material contained in a vaporization chamber of the housing to produce a vaporized material;

a light sensor configured to measure an intensity of light transmitted across the vapor channel and produce sensor data representing the measured intensity;

a measurement circuit in electric communication with the vaporizing element, the measurement circuit configured to produce fluctuation data representing fluctuations in one or both of the resistance and the impedance of the vaporizing element and;

a processor in communication with the light sensor and measurement circuit, wherein the processor:

receives the sensor data for an operating time during which vaporized material flows through the vapor channel;

determines, based on the sensor data, a concentration of a medicament within the vaporized material;

receives the fluctuation data from the measurement circuit;

determines, based at least in part on the determined concentration and the fluctuation data, a dosage of the medicament; and performs at least one action based on the dosage.

* * * * *